United States Patent [19]

Veenstra

[11] Patent Number: Plant 7,629

[45] Date of Patent: Aug. 27, 1991

[54] LILY PLANT NAMED BURNSIDE

[75] Inventor: Rien Veenstra, Wilsonville, Oreg.

[73] Assignee: Oregon Bulb Farms, Inc., Aurora, Oreg.

[21] Appl. No.: 513,482

[22] Filed: Apr. 23, 1990

[51] Int. Cl.[5] ..... A01H 5/00

[52] U.S. Cl. ..... Plt./68

[58] Field of Search ..... Plt. 68, 87.4

[56] References Cited

U.S. PATENT DOCUMENTS

P.P. 4,879 8/1982 McRae ..... Plt. 68
P.P. 6,376 11/1988 McRae ..... Plt. 68
P.P. 6,572 1/1989 McRae ..... Plt. 68
P.P. 6,574 1/1989 McRae ..... Plt. 68
P.P. 6,658 3/1989 McRae ..... Plt. 68

*Primary Examiner*—Howard J. Locker
*Attorney, Agent, or Firm*—Charles W. Rummler

[57] ABSTRACT

A new Asiatic hybrid lily variety of the chalice type particularly distinguished by its very large flowers having a bright Indian orange coloration, in general, borne in raceme arrangement at the upper portion of a strong, upright stem having an average height of about 120 to 140 cm. and abundant foliage; each plant blooming once anually and profusely at mid-season, each flower being borne on a strong, upright pedicel having a length of about 5.5 to 10 cm., in average, spaced axially along the main stem and the buds opening successively as they approach the top of the main stem.

1 Drawing Sheet

BACKGROUND OF THE NEW PLANT

This new lily plant originated as a hybrid seedling resulting from a crossing of the variety Tribute (U.S. Plant Pat. No. 6,003) with pollen from an unnamed and unpatented variety number A-86-BZ selected for a collection of lily plants maintained for breeding purposes, the object of this crossing being the production of tall, high bud count, upright, orange colored Asiatic lilies. The present seedling was selected by me for propagation because of the brilliant orange coloration of its blooms and its tall vigorous growth habit and propagation of this plant was done under my direction at Sandy, Oreg. by means of scaling as well as tissue culture with such success that such propagation was carried on through several successive generations which demonstrated clearly that the novel characteristics of this plant will hold true from generation to generation and appeared to be firmly fixed. This plant is now being propagated by tissue culture and scaling at Aurora, Oreg.

DESCRIPTION OF THE DRAWING

This new variety of lily plant is illustrated by the accompanying full color photographic drawing which shows the upper portion of a full grown blooming plant with fully opened blooms and a plurality of buds at successive ages, the color rendition being as nearly true to that herein specified as can be reasonably obtained by conventional photographic procedures.

DESCRIPTION OF THE NEW PLANT

The following is a detailed description of my new variety of lily as observed at Aurora, Oreg, with color designations according to the R.H.S. Color Chart published by The Royal Horticultural Society of London, England.

THE PLANT

Origin: Seedling.

Parentage:

*Seed parent.*—Lilium Tribute (U.S. Plant Pat. No. 6,003).

*Pollen parent.*—An unnamed and unpatented variety bearing the number A-86-BZ selected from plants maintained at Sandy, Oreg. for breeding purposes.

Classification:

*Botanic.*—Division — 1A, UPR Asiatic hybrid lily.

*Commercial.*—Hybrid Lilium clone.

Form: A tall, erect and stately single stem.

Height: About 120 to 140 cm.

Growth: Vigorous, upright and very strong.

Foliage:

*Quantity.*—Abundant.

*Size of leaf.*—8 to 16 cm. long and about 1 to 1.5 cm. wide.

*Shape of leaf.*—Linear with entire margins.

*Texture.*—Leathery.

*Color.*—Upper side — Dark Green. Under side — A somewhat lighter Green.

Bulbs:

*Size.*—Ranging to 25 cm. in circumference for commercial use.

*Color.*—White.

THE BUD

Shape: Long oblong.

Size: About 2.5 cm. in diameter and about 9 cm. in length.

Rate of opening: The bud opens slowly at maturity in response to light.

Color:

*When tepals first divide.*—Orange Red 30-A.

*When tepals begin to unfurl.*—Orange Red 30-A.

Peduncle:

*Length.*—About 50 cm.

*Character.*—Strong and erect.

*Color.*—Yellow Green 147-A to 146-B.

Number of buds: Usually one on each pedicel.

THE FLOWER

Blooming habit: Once annually and profusely at mid-season.

Size of flower: Very large.

*Diameter.*—About 14 cm.
*Depth.*—About 7 cm.

Borne: On individual pedicels spaced axially of the main stem to the top where the inflorescence breaks into an umble cluster of about three pedicels each with one bloom.

Shape:
*When bloom first opens.*—Cup shaped.
*When bloom matures.*—A flattened cup.

Tepalage:
*Number.*—Six.
*Arrangement:* Hexagonally and imbricated, the inner (upper) group of three alternating with the group of the outer tepals.
*Form.*—Elliptical with entire margins and acute apex.
*Texture.*—Leathery.
*Aspect.*—Shiny.
*Color.*—Outer tepals — body, Orange Red 32-B with Orange 28-A at the base. Reverse side — Orange Red 30-C. Inside tepals — body, Orange Red 32-A with Orange 28-A at the base. Reverse side — Orange Red 32-A.

Pedicel:
*Length.*—About 5.5 to 10 cm.
*Character.*—Strong and upright, ascending upwardly to about 30° above horizontal.

Discoloration after full bloom: Outer tepals may fade slightly to 32-C, inside tepals may fade slightly to 32-B.

Persistence: The flowers tend to hang on and dry.

Fragrance: None.

Disease resistance: Resistant to fusarium and virus tolerant as observed at Aurora, Oreg.

Lasting quality: About three weeks on the plant and about two weeks as a cut flower.

THE REPRODUCTIVE ORGANS

Stamens:
*Number.*—Six.
*Arrangement.*—Typical of genus Lilium.
*Anthers.*—Size: About 1 cm. Color: Orange-Red 34-C.
*Filaments.*—Length: About 4.5 cm. Color: Orange-Red 30-D.
*Pollen.*—Color: Orange-Red 30-C.

Pistils:
*Number.*—1.
*Style.*—Length: About 4 cm. Color: Orange-Red 28-B to 34-B.
*Stigma.*—Color: Red 53-A.

Character of ovaries: Typical of the genus Lilium.

FRUIT

Fertility: The fruit is fertile.

Shape: Ovoid.

Color at maturity: Soft Brown.

This plant most nearly resembles the variety Fore Runner, U.S. Plant Pat. No. 5,981.

I claim:

1. A new and distinct variety of Asiatic hybrid lily plant, substantially as herein shown and described, characterized by its very large flowers of a generally orange-red coloration blooming profusely at a height of about 120 to 140 cm. on strong, upright stems having abundant foliage.

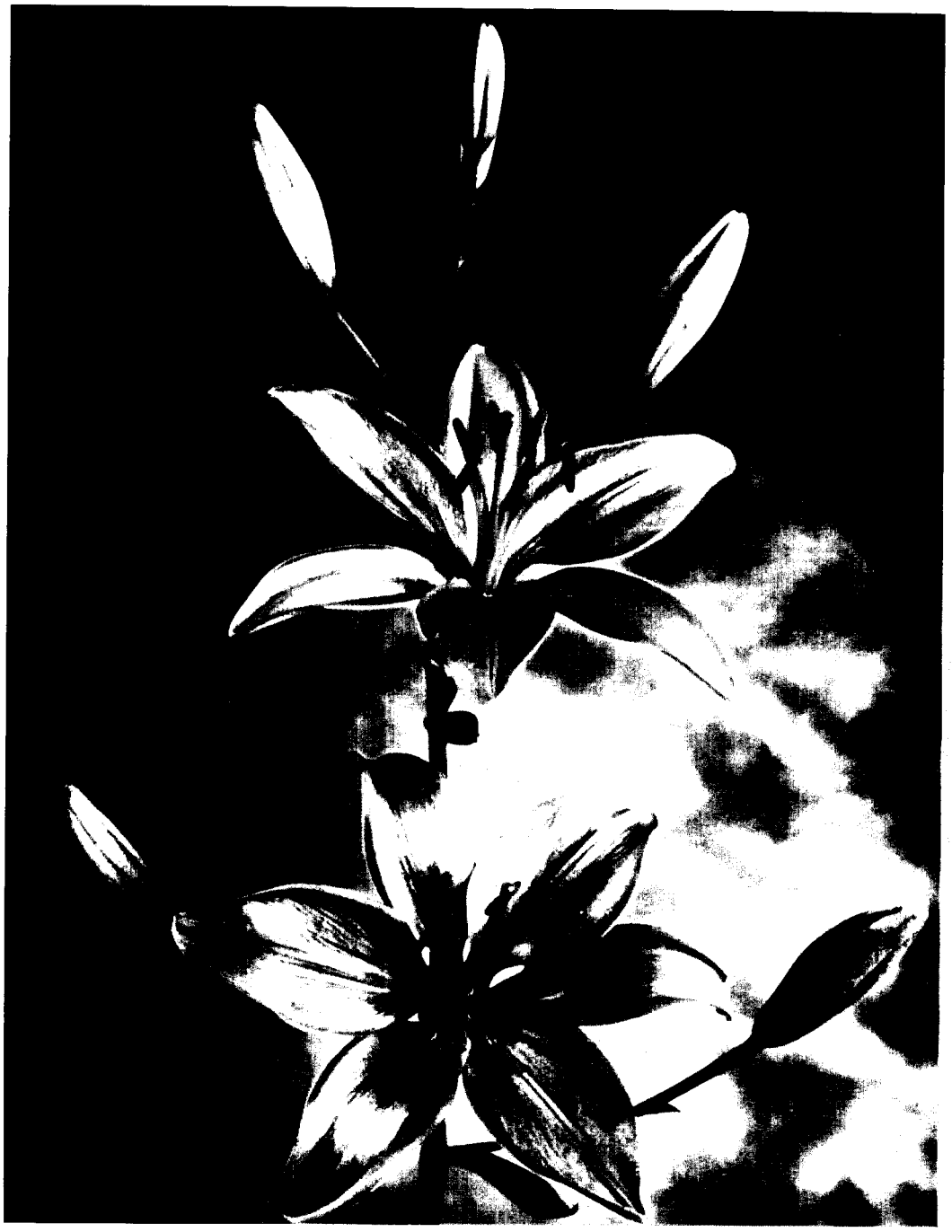

* * * * *